United States Patent [19]

Grisar

[11] 4,206,125

[45] Jun. 3, 1980

[54] 5-[2-[(2,3-DIHYDRO-1,4-BENZODIOXAN-2-YLMETHYL)AMINO]-1-HYDROXYETHYL]-2-HYDROXYBENZOIC ACID DERIVATIVES

[75] Inventor: J. Martin Grisar, Cincinnati, Ohio

[73] Assignee: Richardson-Merrell Inc., Wilton, Conn.

[21] Appl. No.: 36,243

[22] Filed: May 4, 1979

[51] Int. Cl.² ............................................ C07D 319/08
[52] U.S. Cl. .................................. 260/340.3; 424/278
[58] Field of Search ...................................... 260/340.3

[56] References Cited

U.S. PATENT DOCUMENTS

| | | | |
|---|---|---|---|
| 3,686,206 | 8/1972 | Posselt et al. | 260/340.3 |
| 3,883,560 | 5/1975 | Suh et al. | 260/340.5 R |

*Primary Examiner*—Ethel G. Love
*Attorney, Agent, or Firm*—William J. Stein; Eugene O. Retter; George W. Rauchfuss, Jr.

[57] ABSTRACT

Derivatives of 5-[2-[(2,3-dihydro-1,4-benzodioxan-2-ylmethyl)amino]-1-hydroxyethyl]-2-hydroxybenzoic acid are prepared which are useful for their blocking action on α and β-adrenergic receptors. In addition, these compounds are useful as antihypertensive agents.

5 Claims, No Drawings

5-[2-[(2,3-DIHYDRO-1,4-BENZODIOXAN-2-YLMETHYL)AMINO]-1-HYDROXYETHYL]-2-HYDROXYBENZOIC ACID DERIVATIVES

DESCRIPTION

Field of the Invention

This invention relates to 2-[(2,3-dihydro-1,4-benzodioxan-2-ylmethyl)amino]derivatives of 2-hydroxybenzoic acid and their preparation. The compounds are useful as α- and β-adrenergic blocking and hypertensive agents.

SUMMARY OF THE INVENTION

This invention relates to novel 2-hydroxy-5-(1-hydroxy)ethylamine derivatives of benzoic acid. More particularly, this invention relates to certain 2-hydroxy, 2-methoxy and 2-ethoxy derivatives of 5-[2-[(2,3-dihydro-1,4-benzodioxan-2-ylmethyl)amino]-1-hydroxyethyl]benzoic acid or benzamide. Still more particularly, this invention relates to derivatives of 5-[2-[(2,3-dihydro-1,4-benzodioxan-2-ylmethyl)amino]-1-hydroxyethyl]-2-hydroxybenzoic acid having the general formula

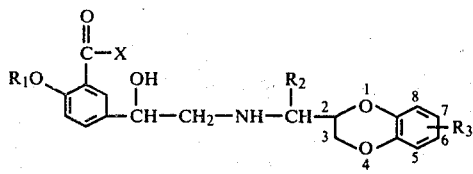

wherein X is selected from the group consisting of hydroxy, methoxy, ethoxy, amino, dimethylamino and alkylamino in which the alkyl group has from 1 to 12 carbon atoms; $R_1$ is hydrogen, methyl and ethyl; $R_2$ is hydrogen and methyl; $R_3$ is selected from the group consisting of hydrogen, methyl, methoxy, fluorine and chlorine; and the pharmaceutically acceptable acid addition salts thereof.

This invention further discloses a method whereby these derivatives may be conveniently prepared in good yield.

DETAILED DESCRIPTION OF THE INVENTION

As seen in general formula (I) above, all of the compounds of this invention contain a 2-[(2,3-dihydro-1,4-benzodioxan-2-ylmethyl)amino]-1-hydroxyethyl moiety attached to the 5-position of the phenyl ring. The remaining two variable groups attached to the phenyl ring, as represented by the symbol X and $R_1$, can include the carboxyl and hydroxyl groups, respectively. Thus, for purposes of uniformity of nomenclature, all of the compounds described herein are designated as 5-[2-[(2,3-dihydro-1,4-benzodioxan-2-ylmethyl)-amino]-1-hydroxyethyl]-2-hydroxy derivatives of benzoic acid.

In addition to the various derivatives of benzoic acid described herein, the corresponding methyl and ethyl esters, as well as certain amides, are also contemplated as being within the scope of this invention. Thus, where the symbol X represents the methoxy and ethoxy groups, the corresponding methyl and ethyl esters of 5-[2-[(2,3-dihydro-1,4-benzodioxan-2-ylmethyl)amino]-1-hydroxyethyl]-2-hydroxybenzoic acid are contemplated.

Where the symbol X represents the amino, dimethylamino and the alkylamino groups, the various substituted and unsubstituted benzamides are delineated. In the case of the N-alkylamino group, the amide nitrogen atom is substituted with an alkyl group having from 1 to 12 carbon atoms. Illustrative of these N-alkyl groups are methyl, ethyl, propyl, butyl, amyl, hexyl, heptyl, octyl, nonyl, decyl, undecyl and dodecyl. Those N-lower alkyl groups having from 1 to 4 carbon atoms delineate the preferred N-alkyl substituted benzamides. Additionally, the various branched and positional isomers of these alkyl groups are included within the scope of this invention so long as the alkyl group is univalent and does not exceed a total of 12 carbon atoms.

The symbol $R_1$ is represented by hydrogen, or the methyl and ethyl groups. Where $R_1$ is hydrogen and X is hydroxy, the compounds can be designated as 5-[2-[(2,3-dihydro-1,4-benzodioxan-2-ylmethyl)amino]-1-hydroxyethyl]salicylic acid. However, for uniformity of nomenclature these compounds will be termed as derivatives of 2-hydroxy-benzoic acid.

As can be further seen in formula (I) above, the phenyl ring of the 2,3-dihydro-1,4-benzodioxan moiety can be substituted or unsubstituted as indicated by the symbol $R_3$. Substitution is limited to the methyl, methoxy, fluorine and chlorine groups, but can take place at the 5,6,7 or 8-positions of the fused benzene ring.

The 2-hydroxybenzoic acids or benzamides of this invention can be regarded as containing a (1-hydroxyethyl)aminomethyl substituent at the 5-position, wherein the terminal methyl group is substituted with a 2,3-dihydro-1,4-benzodioxan-2-yl moiety. Additionally, the terminal methyl group can be further substituted as indicated by the symbol $R_2$. In this case, however, substitution is limited to that of a single methyl substituent.

When the symbol X represents the amino, dimethylamino and alkylamino group in which the alkyl group has from 1 to 12 carbon atoms, a preferred class of benzamides and N-mono-substituted or di-substituted benzamides is delineated within the broad scope of this invention.

A still more preferred group of compounds within the scope of this invention are the 2-hydroxybenzamides, delineated when the symbol X represents the amino group and $R_1$ is hydrogen.

The expression pharmaceutically acceptable acid addition salts encompasses any non-toxic organic or inorganic acid addition salts of the base compounds represented by formula (I). Illustrative inorganic acids which form suitable salts include hydrochloric, hydrobromic, sulfuric and phosphoric acid as well as acid metal salts such as sodium, monohydrogen orthophosphate and potassium hydrogen sulfate. Illustrative organic acids which form suitable salts include the mono-, di- and tri-carboxylic acids, for example, acetic, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid, 2-hydroxyethane sulfonic acid and benzenesulfonic acid. The salts that are formed can exist in either a hydrated or a substantially anhydrous form.

Illustrative specific free base compounds encompassed by formula (I) above include:
5-[2-[(2,3-dihydro-1,4-benzodioxan-2-ylmethyl)-amino]-1-hydroxyethyl]-2-hydroxybenzoic acid,
5-[2-[(5-chloro-2,3-dihydro-1,4-benzodioxan-2-ylmethyl)amino]-1-hydroxyethyl]-2-methoxybenzoic acid, 5-[2-[(2,3-dihydro-6-methyl-1,4-benzodioxan-2-ylmethyl)amino]-1-hydroxyethyl]-2-ethoxybenzoic acid,
5-[2-[[1-(2,3-dihydro-1,4-benzodioxan-2-yl)ethyl]amino]-1-hydroxyethyl]-2-hydroxybenzoic acid,
methyl 5-[2-[(2,3-dihydro-1,4-benzodioxan-2-ylmethyl)amino]-1-hydroxyethyl]-2-hydroxybenzoate,
methyl 5-[2-[(2,3-dihydro-7-methoxy-1,4-benzodioxan-2-ylmethyl)amino]-1-hydroxyethyl]-2-methoxybenzoate,
ethyl 5-[2-[(2,3-dihydro-8-fluoro-1,4-benzodioxan-2-ylmethyl)amino]-1-hydroxyethyl]-2-ethoxybenzoate,
ethyl 5-[2-[[1-(2,3-dihydro-1,4-benzodioxan-2-yl)-ethyl]amino]-1-hydroxyethyl]-2-hydroxybenzoate,
5-[2-[(2,3-dihydro-1,4-benzodioxan-2-ylmethyl)-amino]-1-hydroxyethyl]-2-hydroxybenzamide,
5[2-[(2,3-dihydro-5-fluoro-1,4-benzodioxan-2-ylmethyl)amino]-1-hydroxyethyl]-2-methoxybenzamide
5-[2-[(2,3-dihydro-6-methoxy-1,4-benzodioxan-2-ylmethyl)amino]-1-hydroxyethyl]-2-ethoxybenzamide,
5-[2-[[1-(2,3-dihydro-1,4-benzodioxan-2-yl)ethyl]amino]1-hydroxyethyl]-2-hydroxybenzamide,
5-[2-[(2,3-dihydro-1,4-benzodioxan-2-ylmethyl)amino]-1-hydroxyethyl]-2-hydroxy-N-methylbenzamide,
5-[2-[(2,3-dihydro-7-methyl-1,4-benzodioxan-2-ylmethyl)amino]-1-hydroxyethyl]-2-methoxy-N,N-dimethylbenzamide,
5-[2-[(8-chloro-2,3-dihydro-1,4-benzodioxan-2-ylmethyl)amino]-1-hydroxyethyl]-2-ethoxy-N-propylbenzamide,
5-[2-[(2,3-dihydro-6-fluoro-1,4-benzodioxan-2-ylmethyl)amino]-1-hydroxyethyl]-2-hydroxy-N-hexylbenzamide,
5-[2-[(2,3-dihydro-5-methoxy-1,4-benzodioxan-2-ylmethyl)amino]-1-hydroxyethyl]-2-methoxy-N-nonylbenzamide,
5-[2-[(2,3-dihydro-8-methyl-1,4-benzodioxan-2-ylmethyl)amino]-1-hydroxyethyl]-2-ethoxy-N-dodecylbenzamide, and
5-[2-[[1-(2,3-dihydro-1,4-benzodioxan-2-yl)ethyl]amino]-1-hydroxyethyl]-2-hydroxy-N-methylbenzamide.

The 5-[2-[(2,3-dihydro-1,4-benzodioxan-2-ylmethyl)amino]-1-hydroxyethyl]-2-hydroxybenzoic acid derivatives of formula (I) are readily prepared by condensing a derivative of 2-hydroxy-5-(2-bromoacetyl)benzoic acid (II) with a (2,3-dihydro-1,4-benzodioxan-2-ylmethyl)amine (III). The resulting 2-hydroxy-5-[[(2,3-dihydro-1,4-benzodioxan-2-ylmethyl)amino]acetyl]benzoic acid derivative (IV) is subsequently reduced to the desired derivative of 5-[2-[(2,3-dihydro-1,4-benzodioxan-2-yl)amino]-1-hydroxyethyl]-2-hydroxybenzoic acid (I).

This process may be schematically illustrated as follows:

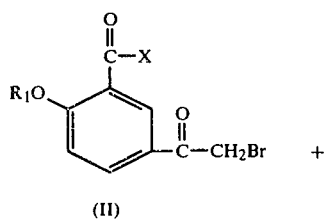

(II)

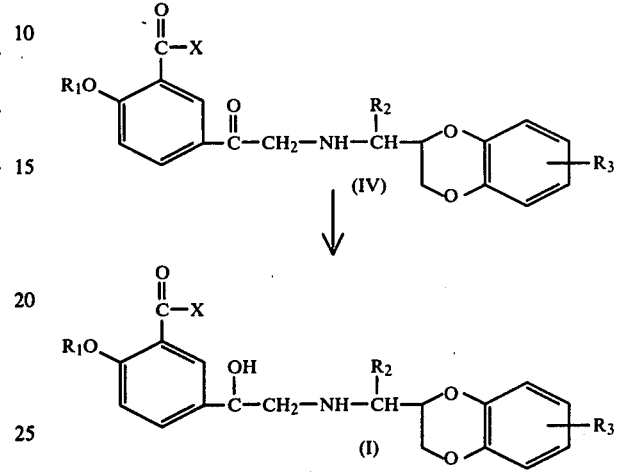

The 2-hydroxy-5-(2-bromoacetyl)benzoic acid derivatives (II) are readily obtained in via the bromination of the corresponding known 2-hydroxy-5-acetylbenzoic acid derivatives. Bromination is conducted in an inert solvent such as chloroform or tetrahydrofuran by the addition of a brominating agent such as bromine, cupric bromide, pyrrolidone-2 hydrotribromide and phenyltrimethylammonium perbromide. Where the symbol X is the methoxy or ethoxy group, the use of bromine is most convenient.

The condensation of the 2-hydroxy-5-[[(2,3-dihydro-1,4-benzodioxan-2-ylmethyl)amino]acetyl]benzoic acid derivatives (IV) is conducted in a suitable anhydrous solvent such as diethyl ether, tetrahydrofuran or dimethylformamide. The resulting hydrobromic acid that is released during the reaction is captured by the 2-hydroxy-5-[[(2,3-dihydro-1,4-benzodioxan-2-ylmethyl)amino]acetyl]benzoic acid derivative (IV) that forms. More conveniently, an equivalent of triethylamine or a base that is stronger in basicity than the 2-hydroxy-5-[[(2,3-dihydro-1,4-benzodioxan-2-ylmethyl)amino]acetyl]benzoic acid derivative (IV) can be added to form a hydrobromide salt which can be readily separated from the reaction mixture.

The condensation reaction proceeds at a reasonable rate at room temperature and is slightly exothermic. Control of the reaction time and temperature is important inasmuch as the carbonyl groups present in the 2-hydroxy-5-(2-bromoacetyl)benzoic acid derivatives (II) and the 2-hydroxy-5-[[(2,3-dihydro-1,4-benzodioxan-2-ylmethyl)amino]acetyl]benzoic acid derivatives that form (IV) can also undergo reactions with the (2,3-dihydro-1,4-benzodioxan-2-ylmethyl)amine resulting in undesirable side products. The condensation can be conducted at a temperature range of from about 0°–50° C. and for a period of time ranging from 1 hour to 3 days. Preferably, a temperature of from 20°–30° C. and a reaction time of from 2 to 16 hours is employed. The slow addition of the 2-hydroxy-5-(2-bromoacetyl)benzoic acid derivatives to the (2,3-dihydro-1,4-benzodioxan-2-ylmethyl)amines is also found to be advantageous.

Reduction of the 2-hydroxy-5-[[(2,3-dihydro-1,4-benzodioxan-2-ylmethyl)amino]acetyl]benzoic acid derivatives (IV) to the corresponding alcohols of the present invention (I) can be achieved using a variety of reagents. Where the symbol X represents the methoxy and ethoxy groups, it is important to use a selective reducing agent that will reduce only the 5-(substituted) acetyl ketone and not the ester or amide functions as well. The reaction can be achieved by hydrogenation in the presence of a noble metal catalyst such as platinum, plladium or rhodium on charcoal. Preferably, a palladium on charcoal catalyst is employed.

Alternatively, a suitable metal hydride reagent may be employed. The choice of the particular hydride reagent to be employed is dependent upon the nature of the symbol X. Thus, where X results in an ester or amide function being present, the reagent must be one that reduces only the desired 5-(substituted)acetyl ketone and not the carbonyl ester or amide function. Where X represents the methoxy or ethoxy group, sodium borohydride in a solvent such as methanol at a temperature of from 0° to 20° C. is preferably employed. In the event that a stereoselective reduction is desired, the use of certain highly hindered lithium or potassium trialkylborohydride reagents may be favorably employed as for example lithium B-isopino-campheyl-9-borabicyclo[3.3.1]nonyl hydride, cf., Krishnamurthy et al., J. Org. Chem., 42, 2534 (1977).

In the case where the symbol X represents a carboxyl or an amide function, it may be desirable to first prepare the corresponding methyl or ethyl ester of the 5-[2-[(2,3-dihydro-1,4-benzodioxan-2-ylmethyl)amino]-1-hydroxyethyl]-2-hydroxybenzoic acid derivative desired (I) and subsequently hydrolyze it to the corresponding free acid or convert it to the particular amide desired. Hydrolysis of the methyl or ethyl esters of (I) to the corresponding free acids can be achieved using either aqueous acid or alkali in accordance with standard procedures well known to those skilled in the art.

The conversion of the methyl or ethyl esters (I) to the corresponding amides, N-substituted or N,N-dimethylamide is conducted using an excess of ammonia or the appropriate amine in an alcoholic solvent. Preferably, methanol is employed. If a gaseous amine is employed such as ammonia or methylamine, the reaction temperature should be maintained at 25° C. or lower, unless the reaction is conducted in a suitable closed pressurized vessel. The amide conversion reaction can be facilitated by the use of a catalyst such as sodium methoxide, sodium amide or dimethylaluminum amide (A. Basha et al., Tetrahedron Letters, 1977, pp. 4171-7). In most cases freshly prepared sodium methoxide provides satisfactory results.

The compounds of formula (I) possess $\alpha$ and $\beta$-adrenergic receptor blocking activity and are useful in the treatment or prophylaxis of cardiovascular disorders, as for example arrhythmias, coronary heart disease, angina pectoris and hypertension in mammals. In addition, these compounds possess useful spasmolytic activity in mammals. The term mammals is intended to include inter alia such mammals as mice, rats, guinea pigs, rabbits, ferrets, dogs, cats, cows, horses and primates including man.

The 5-[2-[(2,3-dihydro-1,4-benzodioxan-2-ylmethyl)amino]-1-hydroxyethyl]-2-hydroxybenzoic acid derivatives can be administered as their pharmaceutical salts in combination with a pharmaceutical carrier using conventional dosage unit forms. Suitable dosage unit forms include oral preparations such as tablets, capsules, powders, granules, oral solutions and suspensions, sublingual and intrabuccal preparations, as well as parenteral dosage unit forms useful for subcutaneous intramuscular or intravenous administration.

The amount of the active ingredient to be administered can vary widely according to the particular dosage unit employed, the period of treatment, the age and sex of the patient treated and the nature and extent of the disorder treated. The total amount of active ingredient to be administered will generally range from about 1 mg/kg to 100 mg/kg and preferably from 3 mg/kg to 25 mg/kg. A unit dosage may contain from 25 to 500 mg of active ingredient, preferably from 100 to 250 mg of active ingredient, and can be taken one or more times per day.

The preferred route of administration is via oral administration. Illustrative dosage levels of the active ingredient for oral administration range from 1 to 100 mg/kg of body weight. Preferably from 3 to 25 mg/kg of the active ingredient are orally administered in humans during a 24 hour period. In those instances where the drug is administered by the parenteral route, corresponding lower dosages are usually employed.

Formulations for oral use may be presented as hard or soft shelled gelatin capsules containing only the active ingredient, but generally blended with conventional pharmaceutical carriers or excipients such as gelatin, various starches, lactose, calcium phosphate, or powdered sugar. The term pharmaceutical carrier is intended to include lubricants employed to improve the flow of tablet granulations and to prevent the adhesion of tablet material to the surfaces of tablet dies and punches. Suitable lubricants include, for example, talc, stearic acid, calcium stearate, magnesium stearate and zinc stearate. Also included in the definition of a pharmaceutical carrier as used herein are disintegrating agents added to assist the break up and dissolution of tablets following administration, dyes and coloring agents, and flavoring agents to enhance the aesthetic qualities of the tablets and make them more acceptable to the patient.

Suitable liquid excipients for the preparation of liquid dosage unit forms include water and alcohols such as ethanol, benzyl alcohol and the polyethylene alcohols, either with or without the addition of a surfactant. In general, the preferred liquid excipients include water, saline solution, dextrose and glycol solutions, as for example an aqueous propylene glycol or an aqueous solution of polyethylene glycol. Liquid preparations to be used as sterile injectable solutions will ordinarily contain from about 0.5 to about 25% by weight, of the active ingredient in solution. In certain topical and parenteral preparations, various oils are utilized as carriers or excipients. Illustrative of such oils are mineral oils, glyceride oils such as lard oil, cod liver oil, peanut oil, sesame oil, corn oil, and soybean oil. Where a compound is insoluble in the particular vehicle chosen, suspending agents may be added as well as agents to control viscosity of the solution, as for example, magnesium aluminum silicate or carboxymethylcellulose. In addition to these excipients, buffers, preservatives and emulsifying agents may also be suitably employed.

The proportion of the active ingredient employed in parenteral dosage unit forms ranges from about 0.05 to about 20% by weight, preferably from about 0.1 to about 10% by weight of the total liquid composition, the remaining component or components comprising any of the various pharmaceutical excipients previously disclosed. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above-identified HLB, or a mixture of two or more components having the desired HLB. Illustrative of surfactants used in parenteral formulations are the class of polyoxyethylene sorbitan fatty acid esters as for example, sorbitan monooleate and the high molecular weight adducts of ethylene oxide with a hydrophobic base, formed by the condensation of propylene oxide with propylene glycol.

The invention herein described is more particularly illustrated in conjunction with the following specific Examples, but not necessarily limited thereto.

EXAMPLE 1

Methyl 5-[2-[(2,3-dihydro-1,4-benzodioxan-2-ylmethyl)amino]-1-hydroxyethyl]-2-hydroxybenzoate hydrochloride A solution of 27.3 g (0.1 mol) ofmethyl 5-(2-bromoacetyl)-2-hydroxybenzoate in 125 ml of tetrahydrofuran is added dropwise over a period of 45 minutes to a solution of 33.0 g (0.2 mol) of (2,3-dihydro-1,4-benzodioxan-2-ylmethyl)amine dissolved in 75 ml of tetrahydrofuran at 25°-8° C. The mixture is stirred for approximately 1 hour at 25° C., cooled to 5° C., the precipitated (2,3-dihydro-1,4-benzodioxan-2-ylmethyl)amine hydrobromide is collected via filtration and washed with small portions of tetrahydrofuran. Approximately 250 ml of diethyl ether is added to the filtrate and upon cooling ($-20°$ C.) overnights, the additional precipitate which separates is collected, 23.5 g (96%). The filtrate is evaporated to dryness, dissolved in isopropanol and acidified with one equivalent of 2 N hydrochloric acid. The product which separates is recrystallized from an isopropanol-water mixture (1:1) to yield 21.1 g (55%) of methyl 5-[[(2,3-dihydro-1,4-benzodioxan-2-ylmethyl)amino]acetyl]-2-hydroxybenzoate hydrochloride having a m.pt. of 206°-7° C. (dec.).

A solution of 15.2 g of the compound prepared in this manner dissolved in 900 ml of methanol and 100 ml of water is hydrogenated over 10.0 g of 10% palladium-on-charcoal catalyst using a Parr shaker over a period of 20 hours. The catalyst is removed under nitrogen via filtration and the solvent evaporated to dryness in vacuo. The residue is recrystallized from an isopropanol-water mixture to yield the desired methyl 5-[2-[(2,3-dihydro-1,4-benzodioxan-2-ylmethyl)amino]-1-hydroxyethyl]-2-hydroxybenzoate hydrochloride, having a m.pt. of 195°-6° C. (dec.).

EXAMPLE 2

Methyl 5-[2-[[1-(2,3-dihydro-1,4-benzodioxan-2-yl)ethyl]amino]-1-hydroxyethyl]-2-hydroxybenzoate hydrochloride Following essentially the same procedure as in Example 1, but substituting 1-(2,3-dihydro-1,4-benzodioxan-2-yl)ethylamine, (2,3-dihydro-8-methyl-1,4-benzodioxan-2-ylmethyl)amine, (7-chloro-2,3-dihydro-1,4-dioxan-2-ylmethyl)amine and (2,3-dihydro-7-methoxy-1,4-benzodioxan-2-ylmethyl)amine for the (2,3-dihydro-1,4-benzodioxan-2-ylmethyl)amine above results in the formation of methyl 5-[2-[[1-(2,3-dihydro-1,4-benzodioxan-2-yl)ethyl]amino]-1-hydroxyethyl]-2-hydroxybenzoate hydrochloride, methyl 5-[2-[(2,3-dihydro-8-methyl-1,4-dioxan-2-ylmethyl)amino]-1-hydroxyethyl]-2-hydroxybenzoate hydrochloride, methyl 5-[2-[(7-chloro-2,3-dihydro-1,4-dioxan-2-ylmethyl)amino]-1-hydroxyethyl]-2-hydroxybenzoate hydrochloride and methyl 5-[2-[(2,3-dihydro-7-methoxy-1,4-benzodioxan-2-ylmethyl)amino]-1-hydroxyethyl]-2-hydroxybenzoate hydrochloride, respectively.

Following the same procedure as in Example 1 but substituting 5-(2-bromoacetyl)-2-methoxybenzoate for the 5-(2-bromoacetyl-2-hydroxybenzoate above, results in the formation of methyl 5-[2-[(2,3-dihydro-1,4-benzodioxan-2-ylmethyl)amino]-1-hydroxyethyl]-2-methoxybenzoate hydrochloride.

EXAMPLE 3

5-[2-[(2,3-dihydro-1,4-benzodioxan-2-ylmethyl)amino]1-hydroxyethyl]-2-hydroxybenzamide The compound methyl 5-[2-[(2,3-dihydro-1,4-benzodioxan-2-ylmethyl)amino]-1-hydroxyethyl]-2-hydroxybenzoate hydrochloride (5.0 g) is converted to its free base by the addition of sodium bicarbonate solution and extracted with methylene chloride. The combined organic extracts are evaporated in vacuo and the residue is dissolved in 100 ml of anhydrous methanol. The resulting solution is saturated at 0° C. with gaseous ammonia and a small amount (about 100 mg) of sodium methoxide or sodium metal is added as a catalyst. The reaction mixture is stirred at room temperature for approximately 3 days or until all of the ester is converted to the amide as determined by thin layer chromatography. The solvent is evaporated in vacuo, and the residue is crystallized and recrystallized from methylene chloride to yield 2.7 g of 5-[2-[(2,3-dihydro-1,4-benzodioxan-2-ylmethyl)amino]-1-hydroxyethyl]-2-hydroxybenzamide, having a m.pt. of 160°-2° C. (dec.). The hydrochloride salt is formed by the addition of one equivalent of isopropanolic HCl and is crystallized from an isopropanol-water mixture.

EXAMPLE 4

5-[2-[[1-(2,3-dihydro-1,4-benzodioxan-2-yl)ethyl]amino]-1-hydroxyethyl]-2-hydroxybenzamide Following essentially the same procedure as in Example 3 but substituting methyl 5-[2-[[1-(2,3-dihydro-1,4-benzodioxan-2-yl)ethyl]amino]-1-hydroxyethyl]-2-hydroxybenzoate hydrochloride, methyl 5-[2-[(2,3-dihydro-8-methyl-1,4-dioxan-2-ylmethyl)amino]-1-hydroxyethyl]-2-hydroxybenzoate hydrochloride, methyl 5-[2-[(7-chloro-2,3-dihydro-1,4-dioxan-2-ylmethyl)amino]-1-hydroxyethyl]-2-hydroxybenzoate hydrochloride, methyl 5-[2-[(2,3-dihydro-7-methoxy-1,4-benzodioxan-2-ylmethyl)amino]-1-hydroxyethyl]-2-hydroxybenzoate hydrochloride and methyl 5-[2-[(2,3-dihydro-1,4-benzodioxan-2-ylmethyl)amino]-1-hydroxyethyl]-2-methoxybenzoate hydrochloride for the methyl 5-[2-[(2,3-dihydro-1,4-benzodioxan-2-ylmethyl)amino]-1-hydroxyethyl]-2-hydroxybenzoate hydrochloride above results in the formation of 5-[2-[[1-(2,3-dihydro-1,4-benzodioxan-2-yl)ethyl]amino]-1-hydroxyethyl]-2-hydroxybenzamide, 5-[2-[(2,3-dihydro-8-methyl-1,4-benzodioxan-2-ylmethyl)amino]-1-hydroxyethyl]-2-hydroxybenzamide, 5-[2-[(7-chloro-2,3-dihydro-1,4-benzodioxan-2-ylmethyl)amino]-1-hydroxyethyl]-2-hydroxybenzamide, 5-[2-[(2,3-dihydro-7-methoxy-1,4-benzodioxan-2-ylmethyl)amino]-1-hydroxyethyl]-2-hydroxybenzamide and 5-[2-[(2,3-dihydro-1,4-benzodioxan-2-ylmethyl)amino]-1-hydroxyethyl]-2-methoxybenzamide, respectively.

EXAMPLE 5

5-[2-[(2,3-Dihydro-1,4-benzodioxan-2-ylmethyl)amino]1-hydroxyethyl]-2-hydroxy-N-methylbenzamide Following essentially the procedure of Example 3 but substituting gaseous methylamine, liquid neopentylamine and dodecylamine for the gaseous ammonia above, results in the formation of 5-[2-[(2,3-dihydro-1,4-benzodioxan-2-ylmethyl)amino]-1-hydroxyethyl]-2-hydroxy-N-methylbenzamide, 5-[2-[(2,3-dihydro-1,4-benzodioxan-2-ylmethyl)amino]-1-hydroxyethyl]-N-(2,2-dimethylpropyl)-2-hydroxybenzamide and 5-[2-[(2,3-dihydro-1,4-benzodioxan-2-ylmethyl)amino]-1-hydroxyethyl]-N-dodecyl-2-hydroxybenzamide, respectively.

EXAMPLE 6

The following is illustrative of the α and β-adrenergic blocking activity for the compounds of this invention.

α-Adrenergic receptor blocking activity is determined in vitro by performing cumulative dose-response experiments in the isolated rabbit aortic strip preparation using norepinephrine as the agonist. The contractile response of the rabbit strip preparation in the presence of logarithmically increasing concentrations of the compounds being tested are expressed as percent of the maximal attainable response. Relative antagonistic potency is expressed as a $pA_2$ value. The $pA_2$ is defined as the negative logarithm of the concentration of the antagonist which produces a doubling of the concentration of agonist required to produce a 50% maximal contraction. Following this procedure the $pA_2$ value for the compound 5-[2-[(2,3-dihydro-1,4-benzodioxan-2-ylmethyl)amino]-1-hydroxyethyl]-2-hydroxybenzamide is found to be 6.20. Under similar conditions the reference compound phentolamine has a $pA_2$ value of 7.78.

β-Adrenergic receptor blocking activity is determined in vitro by performing cumulative dose-response experiments in the isolated guinea pig atria preparation using isoproterenol as the agonist. The response (increase in rate) of the guinea pig atria preparation in the presence of logarithmically increasing concentrations of the compounds being tested are expressed as percent of the maximal attainable response. Relative antagonistic potency is expressed as a $pA_2$ value, as defined above. The $pA_2$ value for the compound 5-[2-[(2,3-dihydro-1,4-benzodioxan-2-ylmethyl)amino]-1-hydroxyethyl]-2-hydroxybenzamide is found to be 5.84. Under similar conditions the reference compound, propranolol, has a $pA_2$ value of 8.89.

EXAMPLE 7

The following Example illustrates the antihypertensive activity for the compounds of the present invention.

Antihypertensive activity is determined in spontaneously hypertensive rats (SHR) of the Okomoto-Aoki strain. Systolic blood pressure of the SHR is measured from the caudal artery by means of an indirect method utilizing a photocell transducer/trail cuff occluder system. Time response relationships are determined for each compound following an oral dose of 50 mg/kg. Data are expressed as mm of Hg decrease from control values. Statistical significance is determined using a 2 tailed "t" test comparing drug treatment response values to those obtained from concurrent vehicle treated animals. Under these conditions the compound 5-[2-[(2,3-dihydro-1,4-benzodioxan-2-ylmethyl)amino]-1-hydroxyethyl]-2-hydroxybenzamide lowered blood pressure by 24 mm of Hg one hour following administration of the drug substance.

I claim:

1. A derivative of 5-[2-[(2,3-dihydro-1,4-benzodioxan-2-ylmethyl)amino]-1-hydroxyethyl]-2-hydroxybenzoic acid having the formula

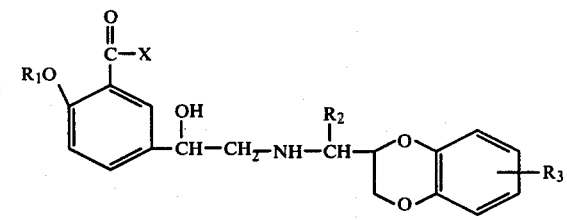

wherein
X is selected from the group consisting of hydroxy, methoxy, ethoxy, amino, dimethylamino and alkylamino in which the alkyl group has from 1 to 12 carbon atoms;
$R_1$ is hydrogen, methyl and ethyl;
$R_2$ is hydrogen and methyl;
$R_3$ is selected from the group consisting of hydrogen, methyl, methoxy, fluorine and chlorine;
and the pharmaceutically acceptable acid addition salts thereof.

2. A compound according to claim 1 wherein X is amino, dimethylamino and alkylamino in which the alkyl group has from 1 to 12 carbon atoms.

3. A compound according to claim 1 wherein X is amino and $R_1$ is hydrogen.

4. A compound according to claim 1 which is methyl 5-[2-[(2,3-dihydro-1,4-benzodioxan-2-ylmethyl)amino]-1-hydroxyethyl]-2-hydroxybenzoate and its pharmaceutically acceptable acid addition salts.

5. A compound according to claim 1 which is 5-[2-[(2,3-dihydro-1,4-benzodioxan-2-ylmethyl)amino]-1-hydroxyethyl]-2-hydroxybenzamide and its pharmaceutically acceptable acid addition salts.

* * * * *